(12) United States Patent
Barsky

(10) Patent No.: US 9,317,817 B2
(45) Date of Patent: Apr. 19, 2016

(54) LIABILITY INTERVENTION LOGISTICAL INNOVATION SYSTEM AND METHOD

(75) Inventor: Lili Loni Barsky, Deerfield, IL (US)

(73) Assignee: Lili Loni Barsky, Deerfield, IL (US)

( * ) Notice: Subject to any disclaimer, the term of this patent is extended or adjusted under 35 U.S.C. 154(b) by 0 days.

(21) Appl. No.: 14/238,654

(22) PCT Filed: Aug. 16, 2012

(86) PCT No.: PCT/US2012/051114
§ 371 (c)(1),
(2), (4) Date: May 7, 2014

(87) PCT Pub. No.: WO2013/025889
PCT Pub. Date: Feb. 21, 2013

(65) Prior Publication Data
US 2014/0247125 A1    Sep. 4, 2014

Related U.S. Application Data

(60) Provisional application No. 61/523,885, filed on Aug. 16, 2011.

(51) Int. Cl.
*G08B 1/08* (2006.01)
*G06Q 10/00* (2012.01)
*G06F 19/00* (2011.01)
*G06Q 50/22* (2012.01)
*G08B 21/24* (2006.01)

(52) U.S. Cl.
CPC .............. *G06Q 10/00* (2013.01); *G06F 19/327* (2013.01); *G06Q 50/22* (2013.01); *G08B 21/245* (2013.01)

(58) Field of Classification Search
CPC ..... G08B 21/245; G08B 21/02; G06F 19/327
USPC .............................. 340/539.12, 539.13, 573.1
See application file for complete search history.

(56) References Cited

U.S. PATENT DOCUMENTS

2011/0291840 A1* 12/2011 Pelland et al. ............. 340/573.1
2012/0112906 A1*  5/2012 Borke et al. ............. 340/539.13
2014/0292518 A1* 10/2014 Wildman et al. .......... 340/573.1

OTHER PUBLICATIONS

International Search Report mailed Dec. 3, 2012 for International Application No. PCT/US2012/051114.
Written Opinion mailed Dec. 3, 2012 for International Application No. PCT/US2012/051114.
(Continued)

*Primary Examiner* — John A Tweel, Jr.
(74) *Attorney, Agent, or Firm* — Dilworth IP, LLC

(57) ABSTRACT

A system and method are disclosed that are able to identify and distinguish persons as soon as they enter or exit a hospital room or any room occupied by a patient who is receiving medical or dental services. After a person who has entered a hospital room has been identified, this person may be required to sanitize his/her hands in order to comply with an established protocol. Therefore, a second identification may take place at the hand sanitization station. The system may confirm that the same person was identified by a first read by the RFID antennas upon entering the room and by a second read by the RFID antennas upon completing the hand sanitization procedure. If no hand sanitization takes place, visual and/or auditory stimuli may be generated as a reminder. Persons and their hand sanitization performances may be used diagnostically to identify and remedy potential contamination events and/or determine the source and mode of transmission of a nosocomial infection. This information may be returned in real-time as well as stored in a database.

16 Claims, 4 Drawing Sheets

(56) References Cited

OTHER PUBLICATIONS

Notice from the European Patent Office dated Oct. 1, 2007 Concerning Business Methods; Official Journal of the European Patent Office; vol. 30, No. 11; Nov. 1, 2007; pp. 592-593; XP007905525.

Statement in Accordance with the Notice from the European Patent Office dated Oct. 1, 2007 Concerning Business Methods—PCT; Nov. 1, 2007; one page; XP002456414.

* cited by examiner

LIABILITY INTERVENTION LOGISTICAL INNOVATION SYSTEM AND METHOD

This application claims the benefit under 35 U.S.C. §371 of International Application No. PCT/US2012/051114, filed Aug. 16, 2012, which claims the benefit of U.S. Provisional Application No. 61/523,885, filed Aug. 16, 2011, which are incorporated by reference herein in their entirety.

BACKGROUND

1. Technical Field

Apparatuses, systems and methods for ensuring compliance hand sanitizing protocols are disclosed. More specifically, this disclosure is directed toward apparatuses, systems and methods for monitoring medical and employee compliance with hand sanitizing protocols.

2. Description of the Related Art

Nosocomial infections, also commonly referred to as hospital acquired infections (HAIs), are infections which may be acquired during a patient's stay in a hospital. HAIs are defined as infections that are acquired 48 hours following admittance into, or 30 days following release from a hospital. HAIs are prevalent throughout the United States; 1.7 million cases of HAI are documented in the US every year. Among the documented cases, 99,000 cases have resulted in death. In addition to this devastating annual death toll, HAIs are also costly from a financial standpoint; costs associated with nosocomial infections reach about $17 billion dollars' annually in the US alone.

Hospitalized patients may be very weak, and are thus more susceptible to infection because their immune systems may be compromised due to the various diseases or conditions from which they are recovering. In fact, studies show that about 1 in 20 patients (~5%) in a US hospital may acquire an HAI during their stay. Furthermore, among critically ill patients in a US intensive care unit (ICU), rate of infection can rise to about 18%. On average, a patient's stay may increase by 12 extra days as a result of an HAI. If the patient acquires multiple HAIs, the average length of stay can be prolonged to about 45 days. With the average cost per day in an American ICU exceeding $3,000 per day, acquiring just one HAI and an additional 12 days in the ICU increases the cost of a hospital stay by over $35,000. If a patient acquires multiple HAIs, the average increase in cost may exceed $1 million. Thus, there is an urgent need to address the rampant spread of HAIs.

HAIs may be transferred to patients via various means in the hospital, but the most common means may be by direct contact between hospital staff and patients. Specifically, because healthcare personnel handle patients carrying different diseases throughout the day, hospital personnel can inadvertently spread residual disease-causing particles merely by making contact with other patients. Additionally, infectious pathogens may be transmitted by contact with contaminated surfaces, also known as fomites. Consequently, hand sanitization has been shown to be one proven method to reduce the spread of diseases such as HAIs due to direct contact. Indeed, the lack of appropriate hand hygiene in US hospitals is believed to be the leading cause of HAIs.

There are several ways by which one may sanitize one's hands. However, one of the most common solutions involves the use of an alcohol-based hand sanitizing solution, or "hand sanitizer". These solutions typically include from about 60% to about 95% alcohol (ethyl alcohol) by volume in the form of a liquid or gel. Hand sanitizers are commonplace throughout hospitals and are used in other locations that are frequented by large numbers of people such as dental offices, business offices, grocery stores, shopping malls, etc. Hand sanitizers are shown to kill 99.5% of transient micro-organisms, when applied to the hands for 15 to 30 seconds. Because of the alcohol content, hand sanitizers have also been found to be more effective than soap and water at eradicating a wide array of micro-organisms.

Using alcohol-based hand sanitizers has been shown to effectively reduce the incidence of HAIs. A study revealed that incorporating alcohol-based hand sanitizers into hospitals reduces HAIs by between about 30% and about 36%. Unfortunately, while hand sanitizers are sufficiently abundant and effective, hospital personnel do not utilize them with sufficient frequency or as required by hospital protocol. Thus, one way to combat HAIs is to target the widespread problem of noncompliance with hand sanitizing protocol. One study conducted by the Society for Healthcare Epidemiology of America found that compliance levels among US healthcare personnel may be as low as 19%. Further, compliance values rarely exceed 40%. As the result, various nationwide organizations have recently sought to develop interventions that would ideally enforce consistent adherence to proper hand sanitization protocol, and effectively raise compliance levels among healthcare workers.

One strategy involves education of healthcare employees in the form of lectures, demonstrations, written materials, and the like. Further, some institutions have engaged in renovations in order to facilitate compliance. For example, renovated hospitals and new hospitals may include the conspicuous placement of hand sanitizer dispensers and personnel protective equipment (PPE) on or in walls next to each room in an ICU or the conspicuous placement of sinks or wash stations in hospital rooms and/or hospital hallways in order to promote increased hand sanitizing compliance.

Feedback to healthcare employees is another technique utilized in order to increase hand sanitization compliance. Such feedback may consist of the observation and evaluation of a healthcare employee's sanitization performance and compliance with appropriate sanitization practices. Reminders may also be utilized as a form of feedback in the form of safety labels, warnings and other postings. Reminders address the tendency of healthcare employees to forget or become too distracted to comply with hand sanitization procedures. Further, the introduction of negative reinforcement in the form of punishment, or positive reinforcement in the form of incentives, has been demonstrated to convey significant effects upon behavior.

The American Society for Microbiology compiled a variety of national studies regarding compliance techniques, in order to determine the relative efficacy of (1) education with feedback, (2) feedback alone, (3) education only and (4) reminders only. The results of this study are shown in FIG. 1. As shown in FIG. 1, the highest increase in compliance (57.3%) resulted from an approach that integrates education and feedback, followed by feedback alone (46.2%). Methods involving education alone and reminders alone led to the least increases in compliance (13.4% and 8.00%, respectively).

However, improvements to the presently existing compliance strategies are still urgently needed. Specifically, although education with feedback, feedback, education and reminders increase compliance levels, the increase or rise is not sufficient because only 100% compliance may provide assurance that the transmission of HAIs via direct contact are being inhibited as much as possible. Further, the currently employed strategies exhibit a duration-limited impact upon compliance that is not reflected in FIG. 1. Regularly repeated feedback can lead to the most sustained increase in compliance behavior, while reminders provide a modest rise in compliance levels, but only in the short-term. Education alone leads to the least sustained effects upon compliance.

Accordingly, improved apparatuses, systems and methods for ensuring compliance with hospital hand sanitization protocols are needed.

SUMMARY OF THE DISCLOSURE

The disclosed systems and methods serve as a compliance intervention technology, and may integrate various strategies into a feedback, reminder, and monitoring system, which may serve as an effective tactic for any one or more of the following: identifying potential contamination events; alerting administrative personnel regarding a potential contamination; activating a decontamination protocol; postulating a cause or source of nonsocomial pathogens; and combinations thereof. The disclosed system and method may be used to track and remedy environmental contamination and more particularly infectious agents in a patient care area. The disclosed system and method may also include trajectory tracking so that evidence of movement by a person in a patient care area and potential contamination can be obtained and decontamination addressed.

The system may be able to identify and distinguish persons as soon as they approach and/or exit the room through the use of identification tags assigned to each person. The identification tags may include radio frequency identification data (RFID) unique to each person. Using an RFID reader and a plurality of RFID antennas, the disclosed system may be able to identify multiple persons at a time, as well as those inside the room and outside the room in the hallway. As an example, there may be four groups of people that the disclosed system should be able to distinguish.

One group includes individuals providing care for a patient ("patient-care individuals"). The patient is located in a room equipped with the disclosed system. Such people will likely have direct contact with the patient and can be contaminated by the patient if an infectious agent or fomite is present or vice versa. Patient-care individuals may be required to practice hand sanitization compliance when entering and leaving the patient area. Proper compliance may be defined by the Occupational Safety and Health Administration (OSHA) and/or the hospital or clinic where the patient is being treated. In each case, the disclosed system can be adapted to the protocol of the hospital/clinic and cover any applicable OSHA regulations. Preferably, each patient-care individual would be assigned an RFID tag and their RFID signal would be individualized to show that they are involved in direct patient contact as this may change which compliance protocol(s) must be followed.

Within the group of patient-care individuals, the number of certain patient-care individuals may be further broken down so nurse:patient ratios may be tracked as the nurse:patient ratio is highly relevant to the risk of infection.

A second group may include individuals who do not have contact with the patient but will enter the room for various reasons. These individuals include janitorial staff, technical staff, supply restocking staff, etc. These individuals may not be required to comply with entry hand washing protocols but may be required to comply upon exiting the room. An RFID tag with data that differs from the data used to identify patient-care individuals may be helpful to segregate this group.

A third group of individuals includes security personnel who have no responsibility for entering into the patient care areas. Tracking of this type of individuals may prevent or identify illegal or unwanted entries in to the patient care areas (e.g., theft, personal invasion, etc.).

A fourth group includes visitors, who have no compliance responsibility other than standard precautions such as masks, etc. A visitor RFID tag may be assigned to detect and track movements of individuals in this group within a patient area or patient room when visiting. Such data would be useful in an investigation of contamination and to monitor the movements and activity of a contaminated individual should the contamination event become more widespread.

In order to fulfill the 'reminder' function, the system may employ an immediate visual stimulus or an auditory stimulus within a given timeframe after the person has entered the room. The stimulus may be a warning light in the room and/or a signal sent to the person's pager and/or cell phone. If the person is compliant, both of these stimuli should immediately be disabled. If the person is noncompliant, the stimuli should be disabled within a given timeframe after the person has entered the room.

The system may be used to identify persons in a database, which can be utilized by the hospital as a monitoring system and in order to document levels of healthcare worker compliance for government oversight purposes.

In one aspect, a system is disclosed for installation into a room for occupancy by at least one patient that is receiving medical services. The room may include a bed, examination table or examination chair. The room may further include an entrance and at least one hand sanitization station. The disclosed system may be used for determining whether a person, who is wearing an identification tag with radio frequency identification (RFID) data, is complying with a hand sanitization protocol after the person enters the room. The system may include a controller linked to an RFID module wherein the RFID module may include a RFID reader that is linked to a plurality of RFID antennas. The RFID antennas may be used for detecting the RFID data from the tag as well as the position of the person in the room and transmitting to the RFID reader a received signal strength indication (RSSI) data signal including the RFID data from the tag and the position of the person in the room. The RFID reader may then send a first signal to the controller identifying the person and the position of the person in the room. A sensor or detector may be disposed at the hand sanitization station and linked to the controller. If the person engages the station, the proximity sensor may transmit a second signal to the controller. If the controller does not receive the second signal within a predetermined time period after receiving the first signal, the controller may generate a reminder signal indicating that the protocol has not been complied with.

The controller may record receiving the first signal and sending of the third signal as a non-compliant event.

In any one or more aspects described above, the controller may record receiving the first signal and receiving the second signal as a compliant event.

In any one or more aspects described above, the plurality of RFID antennas may include three RFID antennas, one of which is disposed near at least one hand sanitization station, one that is disposed near the entrance of the room and another of which is disposed near the bed, examination table or examination chair.

In any one or more aspects described above, the reminder signal may be selected from the group consisting of: illuminating a light disposed on a wall, ceiling or floor of the room; placing a call to a mobile phone belonging to the person; sending a signal to a pager assigned to the person; an combinations thereof.

In any one or more aspects described above, the room may include a plurality of hand sanitization stations and the system may further include a plurality of proximity sensors. Each proximity sensor may be linked to the controller for transmitting a second signal to the controller.

In any one or more aspects described above, the first signal may further include a time stamp.

In any one or more aspects described above, the controller may be linked to a central computer system that records compliant and non-compliant events associated with the person.

In any one or more aspects described above, the room may be further characterized as being selected from the group consisting of a hospital room, an outpatient surgery room, a physician's examination room, a dental office, a dining establishment or any other venue that requires compliance with hand hygiene protocols.

In any one or more aspects described above, the person may be further characterized as being selected from the group consisting of a physician, a dentist, a nurse, a surgeon, a medical assistant, a hospital guest, janitorial staff, a dental assistant, a dental hygienist or another type of employee.

In another aspect, a method is disclosed for determining whether a person, who is wearing an identification tag with radio frequency identification (RFID) data, is complying with a hand sanitization protocol after the person enters a room. The room may be for occupancy by at least one patient that is receiving medical services. The room may include a bed, examination table or examination chair. The room may further include an entrance and at least one hand sanitization station. The method may include the following: when the person approaches the entrance to the room, detecting the RFID data from the tag as well as the position of the person at the entrance to the room; transmitting a first signal identifying the person and a current position of the person to a controller; if the person visits the hand sanitization station, detecting the presence of the person at the hand sanitization station and transmitting a second signal to the controller indicating that the person has been at the hand sanitization station; if the person does not visit the hand sanitization station within a predetermined time period after the first signal is transmitted, generating an audio or visual reminder; and tracking the position of the person in the room and if the person does not visit the hand sanitization station before approaching the bed, examination table or examination chair, generating a reminder signal and if the person does not visit the hand sanitization before approaching the cabinet generating a reminder signal.

DETAILED DESCRIPTION OF THE PRESENTLY PREFERRED EMBODIMENTS

The disclosed system and method were developed to monitor and enforce hand-washing compliance within a hospital setting using sensors and RFID readers. However, the disclosed system and method is applicable to other medical and dental settings as well as other venues where hand hygiene protocol is enforced. Essentially, the disclosed system and method may be used by dental offices, physician's offices and other settings where medical or dental personnel are interacting with a plurality of patients during the course of a day or shift. The disclosed system and method may be used in conjunction with additional patient interaction data in order to evaluate for and remedy potential environmental contamination events. The disclosed system and method may further be utilized in the investigation of a nosocomial infection, by providing information regarding subject trajectory throughout a room and postulating possible modes of transmission of the infectious pathogen. The application may be designed as a console application and may be run on most conventional operating systems.

Figure 1:
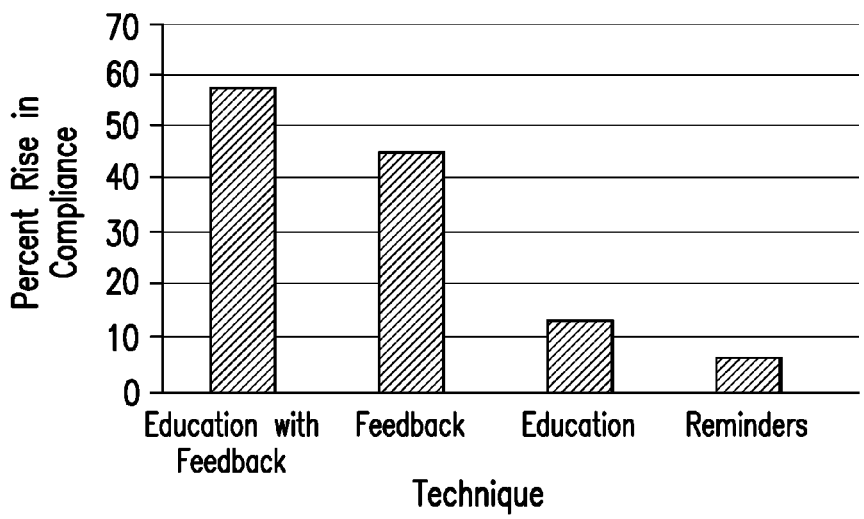
FIG. 1 illustrates, graphically, compliance rates vs. the use of education with feedback, feedback only, education only or reminders only.
Figure 2:
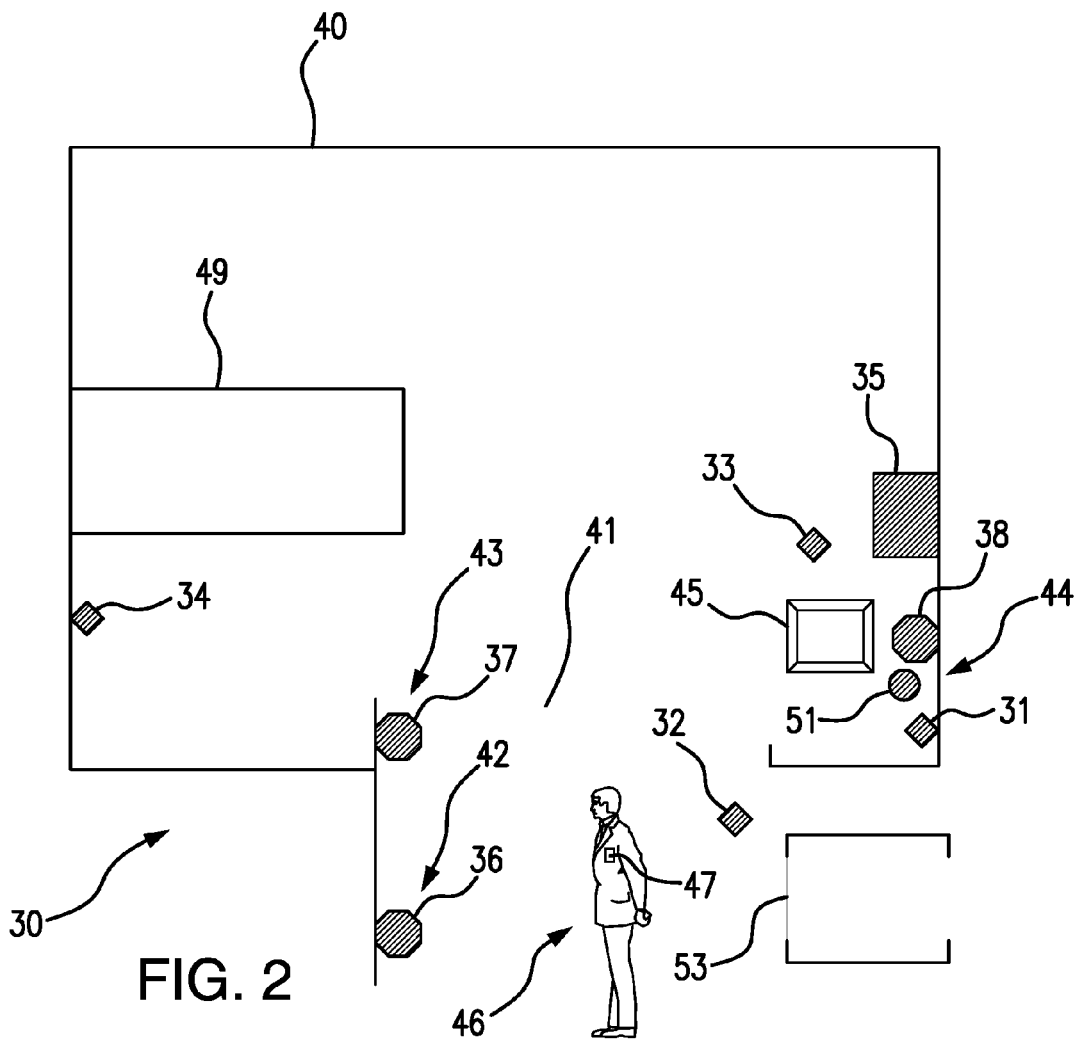
FIG. 2 illustrates, schematically, the incorporation of a disclosed system into a hospital room.

Turning to FIG. 2, the disclosed system 30 and method may support a single RFID reader 31 with unlimited RFID antennas 32, 33, 34 and a single microcontroller or controller 35 with unlimited analog or digital sensors 36, 37, 38 of any type. Support for multiple RFID readers 31 and/or multiple sensor controllers and for digital sensors is possible. The disclosed system 30 and method may use a standard App.config XML-based configuration. This configuration file can be edited in a conventional text editor (e.g., Notepad.exe).

Still referring to FIG. 2, the disclosed system 30 may be installed in a room 40 that includes an entrance 41. The entrance 41 to the room 40 may feature one or more hand sanitization stations 42, 43 that may be in the form of sinks or alcohol sanitizer dispensers. One hand sanitization station 42 may be strategically placed outside the entrance 41 while another hand sanitization station 43 may be disposed at, near or just inside the entrance 41 as shown in FIG. 2. An additional hand sanitization station 44 may be disposed inside the room and may also include a sink 45. Each hand sanitization station 42, 43, 44 may also include a sensor, shown schematically at 36, 37, 38 respectively in FIG. 2. The system is adaptable such that it can be implemented with pre-existing hand sanitation stations. Thus, new hand sanitation stations need not be installed.

Figure 4:
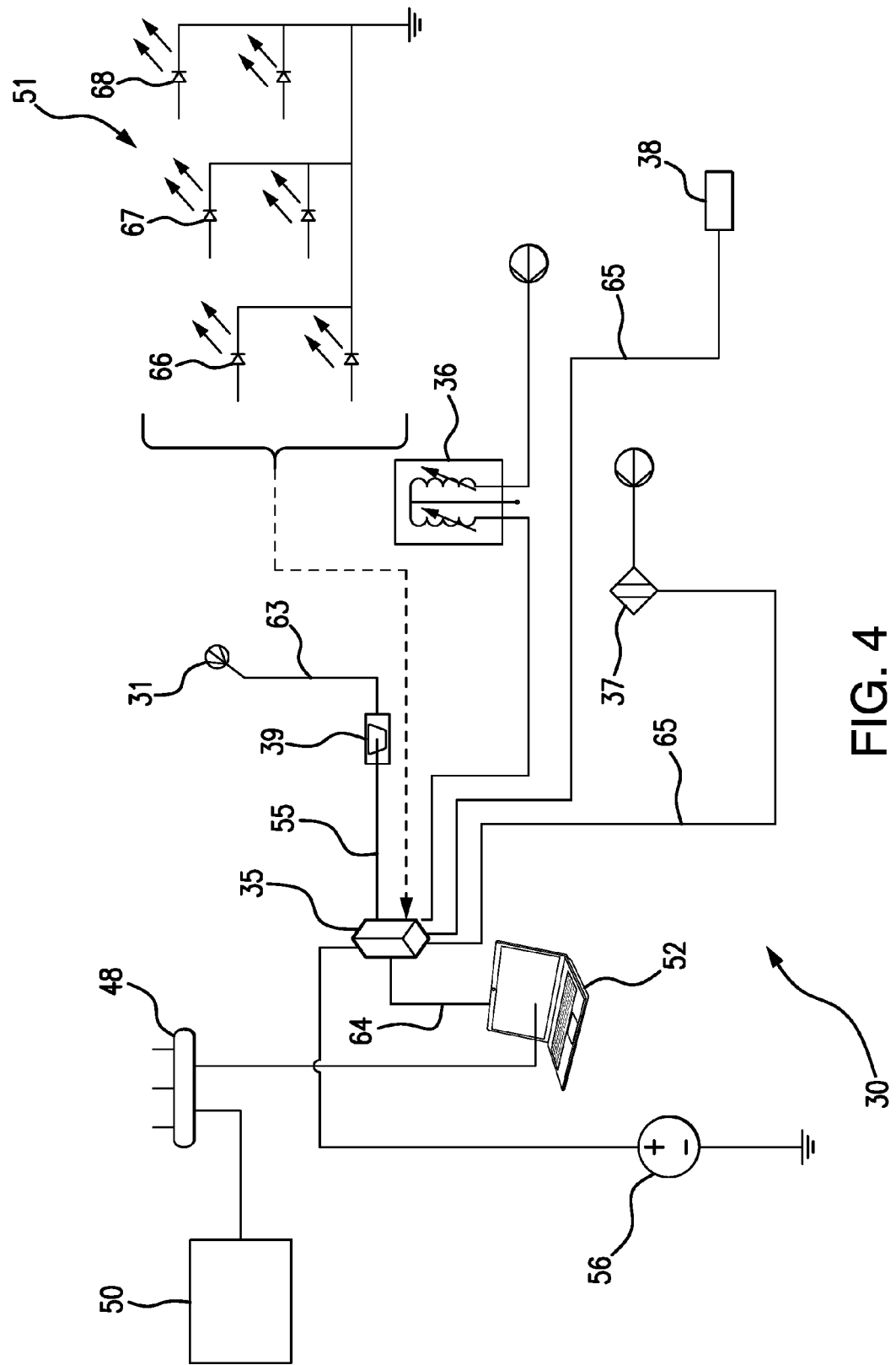
FIG. 4 illustrates, schematically, the connections between the components of the system of FIGS. 2-3.

The combination of the RFID reader 31 and the plurality of antennas 32, 33, 34 enables the system 30 to track the position of a person 46 (i.e., a medical or dental worker or a visitor or guest) just outside the entrance 41 of the room 40, at the entrance 41 of the room 40 and inside the room 40, so long as the person 46 is wearing or carrying a tag 47 with RFID data that can be read by the RFID reader 31 and that preferably identifies the person 46. Therefore, as the person 46 wearing the tag 47 approaches the entrance to the room 40, radio waves emitted by the antennas 32, 33, 34 may interact with the RFID tag 47 and data from the tag 47 may be transferred to the reader 31 in the form of an identification of the person 46, an RSSI value indicative of the person' position and a time stamp. The reader 31 may then interpret the RSSI values from the antennas 32, 33, 34 and determine the position of the person 46 before transmitting the data to the controller 35. The process may be repeated continuously to track the position of the person 46. Thus, if the person 46 passes the hand sanitization station 42 without using the station 42 (and therefore activating the sensor 36), the controller 35 will initiate a timer and the person 46 has a predetermined time period to use one of the hand sanitization stations 42, 43, 44 before he/she approaches the bed 49 (or examination table or examination chair). If the person 46 either approaches the bed 49 before stopping at one of the hand sanitization stations 42, 43, 44 and activating one of the sensors 36, 37, 38, a non-compliant event may be recorded by the controller 35. The controller 35 may initiate a reminder signal that may be sent to the person's pager or mobile phone and/or the controller may activate a reminder mechanism disposed within the room 40, such as a reminder lamp or light 51. Conversely, if the person 46 stops at one of the hand sanitization stations 42, 43, 44 and activates one of the sensors 36, 37, 38, a compliant event may be recorded by the controller 35. Non-compliant events or compliant events may be recorded by the controller 35 or transmitted to a computer 52 for recordation as shown in FIG. 4. The computer 52 may be linked to a local area network (LAN) 48, which may connect the computer 52 to a mainframe computer or central database 50. As an alternative, the controller 35 may be linked directly to the LAN 48 and central database 50 without needing the computer 52.

Returning to FIG. 2, the positions of the antennas 32, 33, 34 may be altered, depending on the configuration of the room 40. Instead of the three antenna configuration of FIG. 2, as few as two antennas 32, 33, 34 or more than three antennas 32, 33, 34 may be used. Further, the tracking of the position of the person 46 may also include tracking the movements and interactions of the person 46 relative to hard and soft surfaces that may be susceptible to contamination, such as the cabinet 53 or sink 45. Thus, if the person 46 makes movements consistent with someone engaging the cabinet 53 or sink 45 after activating one of the sensors 36, 37, 38 at one of the hand sanitization stations 42, 43, 44, the timer may be restarted and a non-compliant event may be recorded even though the person 46 has used one of the hand sanitization stations 42, 43, 44. This feature is important in terms of changing bad habits that the person 46 may have developed over time without realizing the danger to the patient and may also be helpful in terms of training medical and dental personnel.

The tag 47 worn by the person 46 may be issued by the employer of the person 46 or the person 46 may be a guest or visitor. If the latter is the case, the tag 47 may be in the form of a paper or plastic name tag with RFID data embedded therein. A more durable construction may be desirable if the person 46 is a health care worker. The RFID data may be provided in printed form or in the form of a chip as will be apparent to those skilled in the art.

Figure 3:
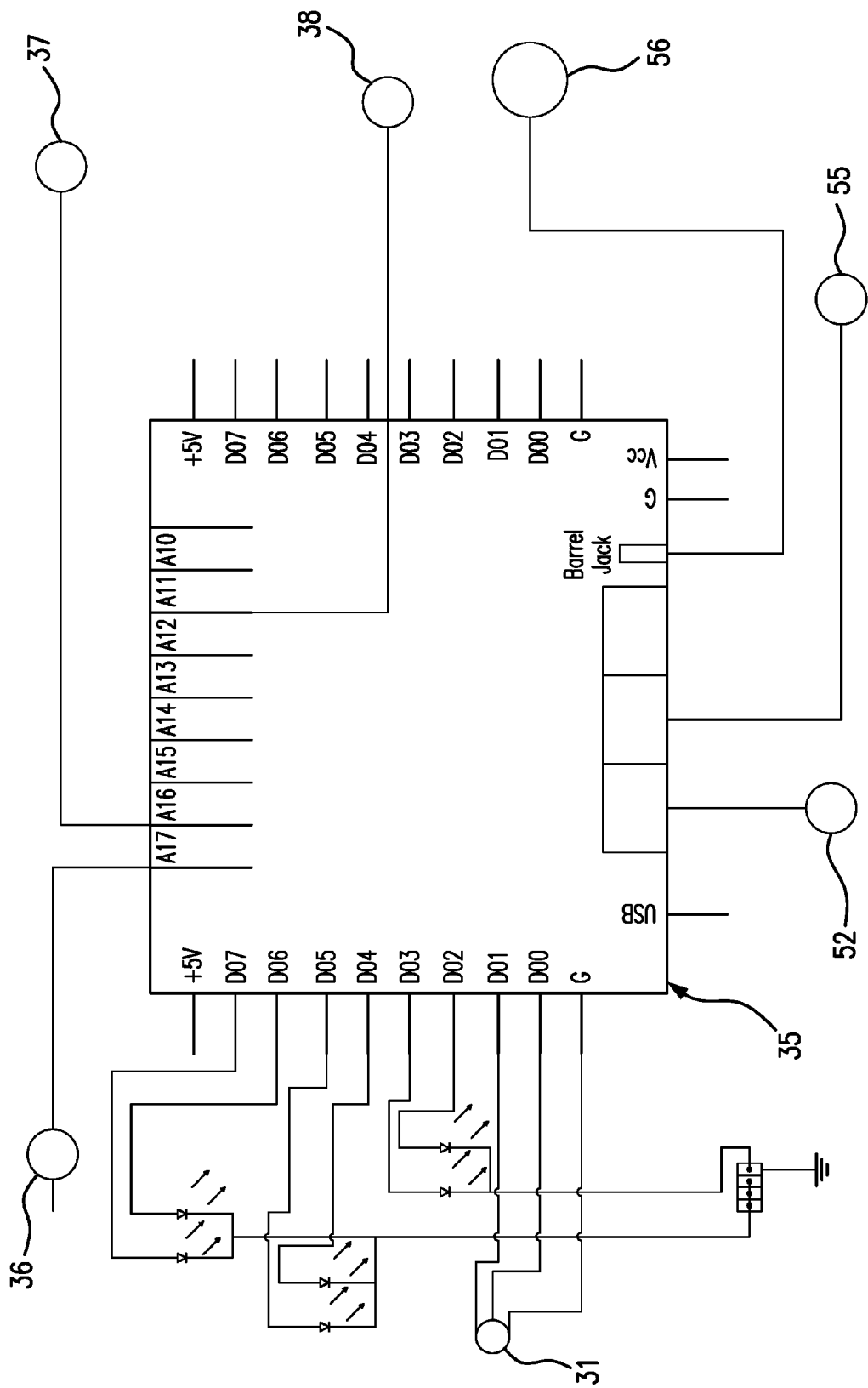
FIG. 3 illustrates, schematically, a controller for use in the system of FIG. 2 and the connections between the controller and the RFID reader, sensors/detectors and a computer such as a personal or a mainframe computer.

Turning to FIG. 3, a schematic diagram of the controller 35 is shown. The controller 35 may be linked to the RFID reader 31 as well as the sensors 36, 37, 38 as shown. Further, the controller 35 may also be linked to the computer 52, a serial port cable 55, which may be connect to the RFID reader 31 as shown in FIG. 4. The controller 35 may also be linked to a 12V adapter 56.

FIG. 4 illustrates the interaction between the complements of the system 30. As noted above, the controller 35, in addition to being linked to the 12V adapter 56, may also be linked to the computer 52, which may be a personal computer or a mainframe computer as noted above. FIG. 4 also shows that the controller 35 may also be linked to the RFID reader 31 and the sensors 36, 37, 38 (see also FIG. 3). The controller 35 may also be linked to a reminder light 51.

Figure 5:
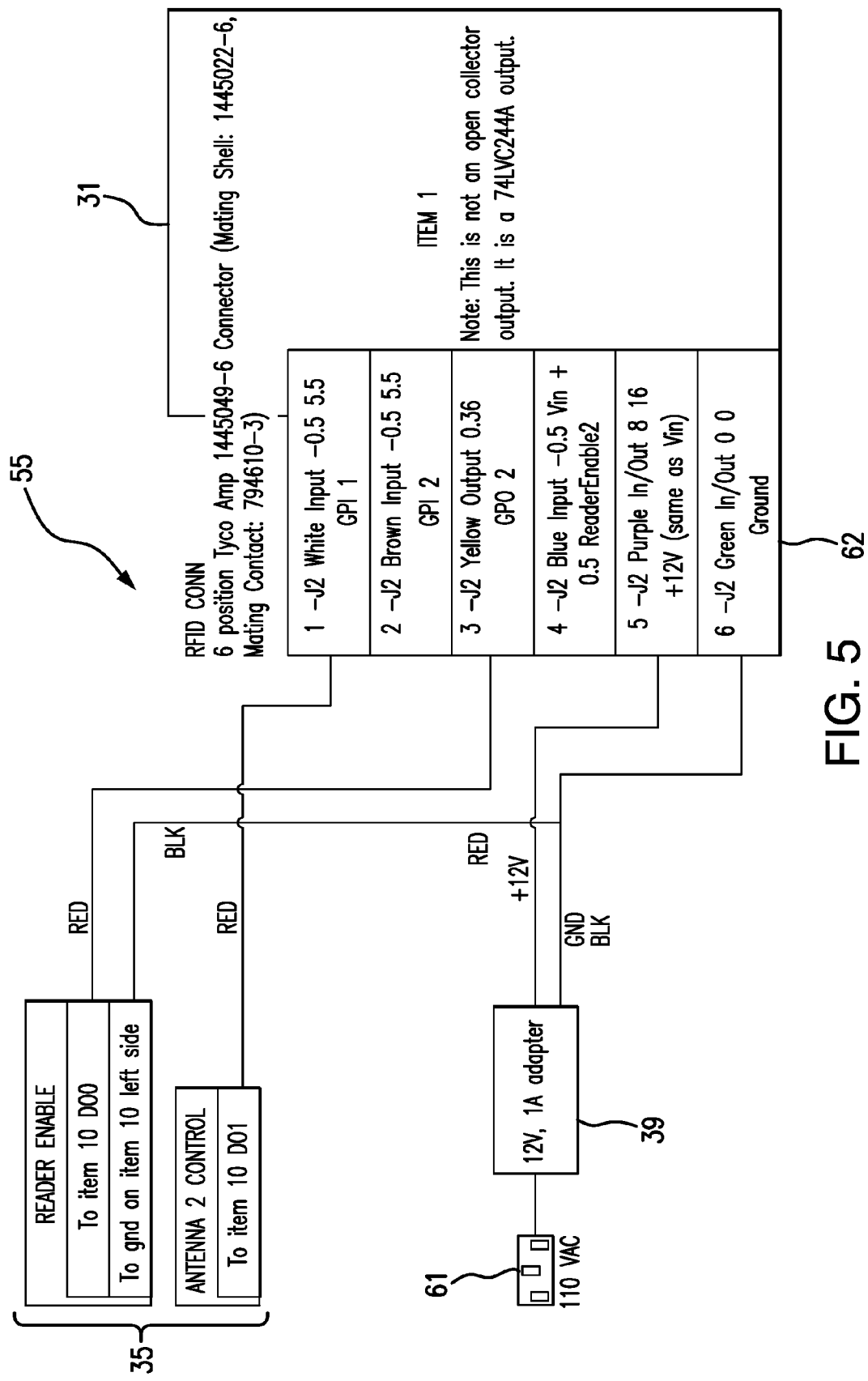
FIG. 5 illustrates, schematically, the power cable construction for the RFID reader of FIGS. 2-4.

Turning to FIG. 5, the construction of the RFID power cable 55 is shown. The cable 55 links the controller 35 to the RFID reader 31. The reader 31 may also be coupled to its own power source by way of the AC-12V adapter 39. The controller 35 and power source 61 may be linked to the RFID reader 31 by way of a six position connector 62.

Application Configuration File

The parameters which can be set in the application configuration file are as follows (also see a complete, commented example configuration in the Sample Configuration File presented immediately below).

key="ReaderURI"—The port that the RFID reader 31 is attached to (if connected to a serial port, this will typically be "tmr:///com1" or "tmr:///com2". If using a USB-to-Serial cable 55 and adapter 39, then this will typically be "tmr:///com3" or "tmr:///com4".)

key="Sensor#"—Each of the sensors 36, 37, 38, which are attached to the controller 35 has a unique number index (typically 0 through 7). For each sensor 36, 37, 38, this value denotes the normal operating values for that sensor 36, 37, 38 and the threshold at which the sensor 36, 37, 38 should be considered "triggered." In one embodiment, the sensor 37 is a 4-30 cm IR sensor and the sensor 38 is a 1 cm diameter force sensor. The calibration curves for the sensors 37, 38 are included in the comments of this file for reference purposes.

key="SensorProfile#"—For each of the sensors 36, 37, 38, specify the location within the room at which the sensor 36, 37, or 38 is located based on the relative readings by each of the antennas 32, 33, 34. All values should be specified as noted in the comments of the configuration file using the RSSI values (in dBm) when a tag is located at the location within the room 40 of the sensor 36, 37, or 38. Although these profiles are not required for the application to run, failure to set them correctly may negatively impact the ability of the system 30 to disambiguate between multiple tags 47 during a sanitization event.

key="Antenna#"—For each of the antennas 32, 33, 34, one can optionally specify the functional location within the room 40 where the antenna 32, 33, or 34 is located.

The remaining configuration keys denote the various timing configurations supported by the system. The Sample Configuration File presented below for a complete example.

---

Sample Configuration File

```
<?xml version="1.0" encoding="utf-8" ?>
<configuration>
    <configSections>
        <section name="log4net"
                 type="log4net.Config.Log4NetConfigurationSectionHandler, log4net" />
    </configSections>
    <appSettings>
        <!-- The URI of the port connected to the RFID reader 31
             (e.g. "tmr:///com4"). -->
        <add key="ReaderURI" value="tmr:///com3" />
        <!-- For each Phidgets sensor, the value is a string containing 3 colon-
             separated numbers.
             o    The first number is the minimum value at which the sensor can
                  accurately read (for 30cm IR this is 80).
             o    The second number is the threshold at which the sensor should be
                  considered "activated" (see chart below).
             o    The third number is the maximum value at which the sensor can
```

-continued

```
                accurately read (for 30cm IR this is 530).
    Thresholds:
        o       For 30cm IR, distance corresponds to ROUGHLY the following thresholds:
                    ■  30 cm away: threshold of 80 (the minimum accurate value for
                       this sensor)
                    ■  25 cm away: threshold of 94
                    ■  20 cm away: threshold of 115
                    ■  15 cm away: threshold of 150
                    ■  12 cm away: threshold of 184
                    ■  10 cm away: threshold of 219
                    ■  9 cm away: threshold of 242
                    ■  8 cm away: threshold of 270
                    ■  7 cm away: threshold of 308
                    ■  6 cm away: threshold of 357
                    ■  5 cm away: threshold of 426
                    ■  4 cm away: threshold of 530 (the maximum accurate value for
                       this sensor)
        o       For 1cm diameter force sensors, pressure corresponds to ROUGHLY the
                following thresholds:
                    ■  0 PSI: threshold of 0 (the minimum accurate value for this
                       sensor)
                    ■  1 PSI: threshold of 130
                    ■  2 PSI: threshold of 245
                    ■  3 PSI: threshold of 360
                    ■  4 PSI: threshold of 475
                    ■  5 PSI: threshold of 600
                    ■  6 PSI: threshold of 715
                    ■  7 PSI: threshold of 830
                    ■  8 PSI: threshold of 940
                    ■  8.25 PSI: threshold of 1000 (the maximum accurate value for
                       this sensor)
    -->
<add key="Sensor1" value="0:600:1000" />
<add key="Sensor3" value="80:357:530" />
<add key="Sensor4" value="80:357:530" />
<!-- For each sensor, the profile value is a string containing colon-separated
    numbers. Each number corresponds to the typical RSSI value (in dBm) read
    by each numbered antenna when a tag is located at that sensor's location.
    For example, at Sensor2, if a tag is typically read with an RSSI of -25 by
    antenna #2, -15 by antenna #3, and typically has no reading by antenna #1,
    then the value of "SensorProfile2" would be ":-25:-15" (note that there is
    no value in the "1" position).
    Note also that dBm values are typically negative (where the stronger the
    signal is, the closer to zero the value becomes) for __passive__ RFID tags.
    -->
<add key="SensorProfile1" value="-35:-32:" />
<add key="SensorProfile3" value=":-23:-35" />
<add key="SensorProfile4" value="-32::" />
<!-- For each antenna, the position value is one of the following strings:
        o       "entrance" - the antenna monitors the entrance of the room only (not
                the room interior)
        o       "inside" - the antenna monitors the interior of the room
        o       "patient" - the antenna monitors the area of the room where the
                patient is located
        o       "enforced" - the antenna monitors the area of the room where the
                patient is located *and* anyone entering that area must be compliant
        o       "compliance" - the antenna monitors an area where anyone entering it
                immediately becomes compliant (e.g. a decontamination shower)
    Any antennas which do not have an explicit sensor position defined for
    them are assumed to be "inside" antennas.
    Note: When the system is in "rounds mode," then "patient" antennas are
    treated as "enforced" antennas (i.e. anyone entering the area must be
    compliant or the lights will begin flashing immediately). When the system
    is *not* in "rounds mode," then "patient" antennas are treated as "inside"
    antennas (i.e. the timer continues counting down until EnterGrace has
    expired, then the lights begin flashing).
    Note: Although sensors are numbered starting at "0", antennas are numbered
    starting at "1".
    -->
<add key="Antenna1" value="entrance" />
<add key="Antenna2" value="inside" />
<add key="Antenna3" value="patient" />
<!-- How long does a person have from when they enter the inside of the room
    (not the entrance) until they must wash their hands (in seconds)? -->
<add key="EnterGrace" value="30" />
<!-- If a person re-enters the room within this many seconds of having left,
    they don't need to rewash their hands. -->
<add key="ExitGrace" value="90" />
<!-- How long can a person stay in the entrance of a room before they are
```

```
                considered "inside" the room (in seconds; -1 = unlimited) -->
            <add key="LingerTime" value="30" />
            <!-- If a person is inside the room, but their tag cannot be read for more than
                this many seconds, assume they left undetected (in seconds; -1 =
                unlimited)
                -->
            <add key="NinjaTime" value="600" />
            <!-- If at least this many people are inside the room at one time, then trigger
                "rounds mode" (0: always in rounds mode; -1 = never in rounds mode) -->
            <add key="RoundsMode" value="5" />
            <!-- How long should the lights flash for to signal non-compliance (in
                seconds)?
                -->
            <add key="FlashLength" value="15" />
            <!-- How fast should the lights flash (in pattern changes per second)? -->
            <add key="FlashSpeed" value="5" />
            <!-- What is the minimum pause between successive non-compliance light
                signaling (in seconds)? -->
            <add key="FlashPause" value="10" />
            <!-- What is the ID of the smallest numbered digital output connected to a
                light (e.g. '0')? -->
            <add key="FirstLightOutput" value="2" />
            <!-- What is the ID of the largest numbered digital output connected to a light
                (e.g. '7')? -->
            <add key="LastLightOutput" value="7" />
        </appSettings>
        <log4net>
            <appender name="LogFileAppender" type="log4net.Appender.RollingFileAppender" >
                <!-- Where to write the log file(s) to. -->
                <param name="File" value="C:\Logs\log.txt" />
                <param name="AppendToFile" value="true" />
                <rollingStyle value="Size" />
                <maxSizeRollBackups value="50" />
                <maximumFileSize value="10MB" />
                <staticLogFileName value="true" />
                <threshold value="DEBUG" />
                <layout type="log4net.Layout.PatternLayout">
                    <param name="ConversionPattern" value="%-5p %d{yyyy-MM-dd hh:mm:ss} - %m%n"
/>
                </layout>
            </appender>
            <appender name="ConsoleAppender" type="log4net.Appender.ConsoleAppender">
                <layout type="log4net.Layout.PatternLayout">
                    <conversionPattern value="%m%n" />
                </layout>
                <threshold value="INFO" />
            </appender>
            <root>
                <level value="DEBUG" />
                <appender-ref ref="LogFileAppender" />
                <appender-ref ref="ConsoleAppender" />
            </root>
        </log4net>
</configuration>
Sample Output Log
```

| | | |
|---|---|---|
| INFO  | 2012-07-19 04:10:19 - | Beginning Initialization... |
| INFO  | 2012-07-19 04:10:19 - | Reading Configuration Settings |
| INFO  | 2012-07-19 04:10:19 - | Completed Initialization... |
| INFO  | 2012-07-19 04:10:19 - | Starting up... |
| INFO  | 2012-07-19 04:10:19 - | (Press Control-C to Exit) |
| DEBUG | 2012-07-19 04:12:18 - | Got reading from tag 29cddcdd89d0934782093723702 on antenna #1 at RSSI of -34 |
| DEBUG | 2012-07-19 04:12:18 - | Handling state change from Entrance to InRoom |
| INFO  | 2012-07-19 04:12:18 - | ENTRANCE: Tag 29cddcdd89d0934782093723702 entered the room |
| DEBUG | 2012-07-19 04:12:18 - | Handling state change from InRoom to InRoom |
| DEBUG | 2012-07-19 04:12:19 - | Got reading from tag 29cddcdd89d0934782093723702 on antenna #2 at RSSI of -23 |
| DEBUG | 2012-07-19 04:12:19 - | Handling state change from InRoom to InRoom |
| DEBUG | 2012-07-19 04:12:20 - | Got reading from tag 29cddcdd89d0934782093723702 on antenna #2 at RSSI of -43 |
| DEBUG | 2012-07-19 04:12:20 - | Handling state change from InRoom to InRoom |
| DEBUG | 2012-07-19 04:12:20 - | Got reading from tag 29cddcdd89d0934782093723702 on antenna #1 at RSSI of -32 |
| DEBUG | 2012-07-19 04:12:20 - | Handling state change from InRoom to InRoom |
| DEBUG | 2012-07-19 04:12:21 - | Got reading from tag 29cddcdd89d0934782093723702 on antenna #3 at RSSI of -31 |
| DEBUG | 2012-07-19 04:12:21 - | Handling state change from InRoom to InRoom |

-continued

| | | |
|---|---|---|
| DEBUG | 2012-07-19 04:12:21 - | Got reading from tag 29cddcdd89d0934782093723702 on antenna #2 at RSSI of −41 |
| DEBUG | 2012-07-19 04:12:21 - | Handling state change from InRoom to InRoom |
| DEBUG | 2012-07-19 04:12:22 - | Got reading from tag 29cddcdd89d0934782093723702 on antenna #3 at RSSI of −32 |
| DEBUG | 2012-07-19 04:12:22 - | Handling state change from InRoom to InRoom |
| DEBUG | 2012-07-19 04:12:22 - | Got reading from tag 29cddcdd89d0934782093723702 on antenna #2 at RSSI of −12 |
| DEBUG | 2012-07-19 04:12:22 - | Handling state change from InRoom to InRoom |
| DEBUG | 2012-07-19 04:12:22 - | Got reading from tag 29cddcdd89d0934782093723702 on antenna #2 at RSSI of −32 |
| DEBUG | 2012-07-19 04:12:22 - | Handling state change from InRoom to InRoom |
| DEBUG | 2012-07-19 04:12:22 - | Got reading from tag 29cddcdd89d0934782093723702 on antenna #1 at RSSI of −42 |
| DEBUG | 2012-07-19 04:12:22 - | Handling state change from InRoom to InRoom |
| DEBUG | 2012-07-19 04:12:22 - | Got reading from tag 29cddcdd89d0934782093723702 on antenna #3 at RSSI of −55 |
| DEBUG | 2012-07-19 04:12:22 - | Handling state change from InRoom to InRoom |
| DEBUG | 2012-07-19 04:12:23 - | Got reading from tag 29cddcdd89d0934782093723702 on antenna #2 at RSSI of −42 |
| DEBUG | 2012-07-19 04:12:23 - | Handling state change from InRoom to InRoom |
| DEBUG | 2012-07-19 04:12:23 - | Got reading from tag 29cddcdd89d0934782093723702 on antenna #2 at RSSI of −42 |
| DEBUG | 2012-07-19 04:12:23 - | Handling state change from InRoom to InRoom |
| DEBUG | 2012-07-19 04:12:24 - | Got reading from tag 29cddcdd89d0934782093723702 on antenna #1 at RSSI of −23 |
| DEBUG | 2012-07-19 04:12:24 - | Handling state change from InRoom to Entrance |
| DEBUG | 2012-07-19 04:12:25 - | Got reading from tag 29cddcdd89d0934782093723702 on antenna #1 at RSSI of −18 |
| DEBUG | 2012-07-19 04:12:25 - | Handling state change from InRoom to Entrance |
| DEBUG | 2012-07-19 04:12:26 - | Got new sensor value of 300 |
| DEBUG | 2012-07-19 04:12:26 - | Got new sensor value of 400 |
| DEBUG | 2012-07-19 04:12:26 - | Above threshold - activated |
| DEBUG | 2012-07-19 04:12:26 - | Got new sensor value of 500 |
| DEBUG | 2012-07-19 04:12:26 - | Above threshold - activated |
| DEBUG | 2012-07-19 04:12:27 - | Got new sensor value of 600 |
| DEBUG | 2012-07-19 04:12:27 - | Above threshold - activated |
| DEBUG | 2012-07-19 04:12:27 - | Got new sensor value of 700 |
| DEBUG | 2012-07-19 04:12:27 - | Above threshold - activated |
| DEBUG | 2012-07-19 04:12:27 - | Got new sensor value of 800 |
| DEBUG | 2012-07-19 04:12:27 - | Above threshold - activated |
| DEBUG | 2012-07-19 04:12:28 - | Got new sensor value of 900 |
| DEBUG | 2012-07-19 04:12:28 - | Above threshold - activated |
| DEBUG | 2012-07-19 04:12:28 - | Got new sensor value of 800 |
| DEBUG | 2012-07-19 04:12:28 - | Above threshold - activated |
| DEBUG | 2012-07-19 04:12:28 - | Got new sensor value of 700 |
| DEBUG | 2012-07-19 04:12:28 - | Above threshold - activated |
| DEBUG | 2012-07-19 04:12:28 - | Got new sensor value of 600 |
| DEBUG | 2012-07-19 04:12:28 - | Above threshold - activated |
| DEBUG | 2012-07-19 04:12:29 - | Got new sensor value of 500 |
| DEBUG | 2012-07-19 04:12:29 - | Above threshold - activated |
| DEBUG | 2012-07-19 04:12:29 - | Got new sensor value of 400 |
| DEBUG | 2012-07-19 04:12:29 - | Above threshold - activated |
| DEBUG | 2012-07-19 04:12:29 - | Got new sensor value of 300 |
| DEBUG | 2012-07-19 04:12:29 - | Log the compliance! |
| INFO | 2012-07-19 04:12:29 - | SENSOR: Tag 29cddcdd89d0934782093723702 activated sensor Sensor4 with maximum value of 900 |
| DEBUG | 2012-07-19 04:12:29 - | Handling state change from InRoom to Compliant |
| INFO | 2012-07-19 04:12:29 - | COMPLIANCE: Tag 29cddcdd89d0934782093723702 sanitized their hands |
| INFO | 2012-07-19 04:12:29 - | LIGHTS: Stop Flashing |
| DEBUG | 2012-07-19 04:12:29 - | Dropped below threshold - no longer active |
| DEBUG | 2012-07-19 04:12:30 - | Got new sensor value of 200 |
| DEBUG | 2012-07-19 04:12:32 - | Handling state change from Compliant to Compliant |
| DEBUG | 2012-07-19 04:12:39 - | Caught Console Interrupt |

Usage

To use the disclosed system 30 and method, as shown in FIG. 4, the controller 35 may be connected to a USB port on a computer 52 (or linked to a network 48 and mainframe computer 50), the RFID reader 31 and the sensors or detectors 36, 37, 38. Using the computer 52 or 50, the configuration application file (as noted above) may be modified to specify the location of the RFID reader 31. The computer 52 or 50 may also be used to update any other configuration settings as necessary to configure the system 30 before launching the application. When launched, the application may search for and connect to the controller 35 and the RFID reader 31 initialize itself based on the configuration settings. Once initialized, the application will enter the execution loop. In one embodiment, pressing Control-C when in the execution window may initiate a clean shutdown of the system 30.

Any important activity that takes place within the system 30 will be logged to the execution window. In addition, verbose logging will be placed in the log file location set in the configuration as well. Each entry in the log file is time-stamped and noted with a "significance level." The significance level of "DEBUG" may be the most verbose output and may be useful for debugging problems. Typically, "DEBUG" is not useful for normal usage. The "INFO" level is where all standard messages are logged. The "ERROR" and "WARNING" levels are only used if a serious error occurs (such as losing connectivity to the RFID reader or sensor controller during operation).

Algorithm

The disclosed system and method monitors hand-washing compliance through tracking the current state of each RFID tag 47 (FIG. 2) detected as the tag 47 progresses within eight (8) different "States", which are recited below:

Not in the Room 40—this is the default state for any tag 47 which is has not yet been detected, or which was last detected too long ago (configurable) and has been purged from the system 30.

In the Entrance 41—a tag 47 is currently located just outside the patient's room 40 in front of the entrance 41 as shown in FIG. 2 and the person 46 has not yet sanitized their hands (but their time window has not yet expired). This state can be achieved both during entry and exit of the room 40.

In the Room 40—a tag 47 is currently located inside of the door or entrance 41 to the patient's room 40 and the person 46 has not yet sanitized his/her hands (but their time window has not yet expired).

Near Patient—a tag 47 is currently located in the vicinity of the patient's bed 49 (or examination table or examination chair) and the person 46 has not yet sanitized his/her hands.

Compliant—a tag 47 is currently anywhere in the room 40 and the person 46 has already sanitized their hands.

Non-Compliant—a tag 47 is currently anywhere in the room 40 and the time window has expired without the person 46 sanitizing their hands (this state is accompanied by a light flash warning). See the reminder light 51 of FIGS. 2 and 4.

Compliant Entrance—a tag 47 is currently just outside the patient's room 40 and the person 46 has already sanitized his/her hands. This state can be achieved both during entry and exit of the room 40.

Non-Compliant Entrance—a tag 47 is currently just outside the patient's room 40 and the time window has expired without his/her sanitizing their hands.

A tag 47 may be transitioned between these states for a number of different reasons. First, based on the relative readings of the antennas 32, 33, 34 for that tag 47, an algorithm detects that the tag 47 has moved between different states (e.g. from In the Entrance to In the Room). Second, a series of timers may be run for each tag 47 and can trigger transitions based on inactivity for an extended period of time. Finally, a transition from non-compliance to compliance is triggered when a sensor 36, 37 or 38 detects a sanitization activity. The tag 47 which is associated with this activity is the tag 47 that is located most closely to the sensor 36, 37 or 38 that was activated (as based on the "Sensor Profiles" that are configured in the application configuration). It is also worth noting that some transitions may be prohibited (e.g. transition from Compliance to Non-Compliance).

The timers which run for each tag 47 are as follows (note: all of them are user-configurable in the application settings):

Linger Time—this is the amount of time that a person 46 can stand in the entrance 41 of the room 40 before they are assumed to have entered the room 40 (and therefore must comply within a predetermined time period).

Exit Grace Time—If a person re-enters the room 40 within this many seconds of having left the room 40, he/she does not need to re-sanitize their hands.

Entrance Grace Time—This is the predetermined time period within which a person can be in the room 40 before they must sanitize their hands. Failure to sanitize within this predetermined time will force the tag into the "Non-Compliance" state.

Ninja Time—If a person 46 has entered the room 40 and has not left through the entrance 41, but has gone undetected by the antennas 32, 33, 34 for a predetermined time period, then the program assumes the person 46 has left the room 40 undetected and must re-sanitize their hands when they are next detected.

Flash Length and Flash Speed—These timers controls how long and how rapidly the reminder light 51 flashes to warn for non-compliance.

Flash Pause—this timer allows for a pause between successive non-compliance flashing sessions (in the event there are multiple non-compliant people 46 within the room 40 at the same time).

"Rounds Mode" can be triggered by more than a set number of people 46 being inside the room 40 at one time. During rounds mode, a tagged person 46 can be inside the room 40 for an unlimited amount of time without becoming non-compliant, but they must have sanitized before entering the vicinity of the patient or the bed 49 (or examination table or examination chair) or else they will immediately become non-compliant.

Data Consolidation and Remote Access

Data collected from each hospital room 40 can be automatically transmitted to a central database for further processing and analysis and assessment of overall subject compliance and contamination. The disclosed system and method may embody an application which manages the database server or mainframe computer 50 and stores all incoming data from the individual rooms 40. The system 30 may also support an application which runs on the database server 50 and provides an interface for interacting with the data stored in the database 50 (both in real-time and retrospectively for reviewing an incident). The disclosed system 30 and method may also include a separate application which runs on the database server 50 and allows for administrative control over the individual rooms 40 in order to dynamically update the room settings or remotely reset the room settings.

Environmental Decontamination

Upon retrieval of data and assignment of compliance status, the disclosed system 30 and method may then integrate and analyze this information in order to evaluate for possible environmental or patient contamination events (PCE), alert the appropriate parties and/or activate a decontamination response.

Patient Contamination Events

If a person 40 interacts with a patient while in the room 40 and fails to comply (i.e. sanitize his/her hands) while in the room 40, or the timestamp of the compliance act is delayed compared to that associated with the patient interaction, the disclosed system 30 and method may document that a potential patient contamination event has occurred. The appropriate parties will then be alerted so that a decontamination response may be deployed.

Other Environmental Contamination Events

This scenario may occur when a person 46 interacts with a key element of his/her environment, such as a supply cabinet 53 (see FIG. 2) prior to entering or while in the room 40. Currently, the disclosed system 30 and method integrates the parameter of linger time with subsequent movement towards or away from the room entrance 41 in order to evaluate for possible noncompliant patient interaction. Namely, if the person 46 has been determined to linger in the entrance 41 and then proceeds to enter the room 40, it will be presumed that the person 46 has interacted with the supply cabinet 53 and it will be documented that he has had "cabinet 53 contact." Alternatively, a sensor (not shown) may be employed in order to detect cabinet 53 usage or movement. Another option would be to place an RFID tag on the door of the cabinet. When the cabinet door changes position, this movement may then be detected by the antennas and documented as cabinet contact. If the person 46 fails to comply or if the timestamp of "cabinet 53 contact" is greater than that associated with the compliance act, the disclosed system 30 and method may document that a potential environmental contamination event has occurred. The appropriate parties will then be alerted so that a decontamination response may be deployed.

Investigation of Nosocomial Infection

In the event of a nosocomial infection, the disclosed system 30 and method may be utilized to consult and assess the trajectories of all subjects 46 who interact with the affected patient, including guests, in order to postulate possible modes by which the infectious pathogen may have been transmitted.

RFID

Radio-frequency identification (RFID) is the use of a wireless non-contact system that uses radio-frequency electromagnetic fields to transfer data from a tag 47 attached to an object, such as a person 46, for the purposes of automatic identification and tracking. Some tags 47 require no battery and are powered by the electromagnetic fields used to read them. Other tags 47 may use a local power source and emit radio waves (electromagnetic radiation at radio frequencies). The tag 47 may contain electronically stored information which can be read from up to several meters away. Unlike a bar code, the tag 47 does not need to be within a line of sight of the RFID reader 31 and may be embedded in the tracked object or tag 47. The RFID reader 31 then records this information and transmits it to a computer 52 or computer system 50.

The RFID reader 31 can read two types of tags: passive and active. The active tags have a battery and generate an identifying signal of their own to the RFID reader 31. This allows for an extended range and can provide more advanced information based upon the location of the tag 47. The passive tags 47 are not powered and use the active signal from the RFID reader 31 for a response, leading to a less extended range. The range for each reader 47 is flexible depending on needs.

RSSI

Received signal strength indication (RSSI) is a generic radio receiver technology metric, which is usually invisible to the user of the device containing the receiver, but is directly known to users of wireless networking of IEEE 802.11 protocol family. RSSI is often done in the intermediate frequency (IF) stage before the IF amplifier. In zero-IF systems, it is done in the baseband signal chain, before the baseband amplifier. RSSI output is often a DC analog level. It can also be sampled by an internal ADC and the resulting codes available directly or via peripheral or internal processor bus.

System Components

The bill of materials for circuit construction and configuration is contained within Table 1 below.

TABLE 1

| Reference Numeral | Part | FIGURE |
| --- | --- | --- |
| 31 | RFID reader | FIGS. 2-5 |
| 39 | AC-12 V adapter | FIG. 2 |
| 55 | Serial port cable | FIG. 2 |
| 63 | Null modem cable | FIG. 2 |
| 37 | 30 cm detector | FIGS. 2-4 |
| 36 | 80 cm detector | FIGS. 2-4 |
| 64 | USB cable | FIG. 2 |

TABLE 1-continued

| Reference Numeral | Part | FIGURE |
| --- | --- | --- |
| 32, 33, 34 | Antenna | FIG. 2 |
| Not shown | Coaxial antenna cable | |
| 35 | Controller (USB/8/8/8 6P HUB) | FIGS. 2-5 |
| 56 | 12 V adapter | FIG. 2 |
| 38 | Force adapter/force sensor | FIGS. 2-4 |
| 65 | Sensor cables | FIG. 4 |
| 66 | Green LED/lens | FIG. 4 |
| 67 | Orange LED/lens | FIG. 4 |
| 68 | Violet LED/lens | FIG. 4 |

The reference numerals in the left column correspond to the reference numerals appearing in FIGS. 2-5.

Integration into a Hospital or Examination Room

As exhibited above, the implementation of the disclosed system 30 may require several components that are positioned throughout a hospital or examination room 40. FIG. 2 illustrates the integrated layout in a standard hospital room 40. Implementation of a wireless microcontroller unit 35 and/or a wireless RFID module 31 is possible, which may automatically transmit data wirelessly to central database 50, whereby data from all units can then be analyzed and compared utilizing system software.

Accounting for Special Circumstances

In addition to the basic functionality outlined above, the disclosed system may also accommodate and make provisions for more unusual situations. In particular, the disclosed system 30 may make adjustments for unique staff members or persons 46. For example, the disclosed system 30 may distinguish between those persons 46 or staff members who must comply each time they enter the room 40 (including nurses, physicians, and the like) and those personnel whose duties may not require them to make patient or environmental contact or who have other sanitization requirements (including cafeteria, janitorial staff, and the like). The disclosed system 30 may also make a provision for monitoring of patient guest compliance, if desired.

For research purposes, the disclosed system 30 may also provide a means by which to assess hand hygiene trends in association with particular room 40 and thus patient information and data.

INDUSTRIAL APPLICABILITY

The benefits of integrating a compliance technology include the following:
Increasing hand washing compliance;
Decreasing HAIs both via reducing the potential for contamination by means of patient contact as well as contact with the patient room environment; and
Decreasing the cost incurred by HAIs.

Increasing Hand Washing Compliance

As mentioned above, the disclosed system 30 should increase hand washing compliance by integrating several tested hand washing compliance intervention technologies into a novel, high tech and cost-effective monitoring system. The first, immediate compliance intervention technology is a non-specific reminder system. The non-specific reminder system provides a visual stimulus that should remind persons who have entered the room to wash their hands. If compliance has not been achieved, an auditory or visual stimulus follows.

Although a consistent reminder system should help improve compliance, as shown above, reminder systems do not increase compliance by a sufficient amount. Thus, a monitoring and feedback system may also be integrated via RFID tagging. Specifically, any person 46 who enters a room 40 with an RFID tag 47 may be identified, and his or her compliance may be recorded. This information may be uploaded into a compliance database on a personal computer 52 and/or central server 50, where person 46 compliance records may be kept and monitored by the hospital administration. By monitoring personnel compliance records in the compliance database, the hospital can also offer feedback to a person 46, a method which has been shown to produce a substantial increase in compliance. Thus, by developing a technology that both continuously monitors a person 46 and provides regular feedback, the effects of increased compliance should not only be achieved but also sustained. Overall, the disclosed system 30 should help perpetuate hand washing compliance at hospitals, outpatient surgical centers, physicians' offices, dental offices, etc.

Decreasing HAIs

By increasing hand washing compliance, the number of HAIs may subsequently drop. Focusing upon the ICU as the area where the system may first be implemented and utilized, the current U.S national rate of nosocomial infection is 5%. Correlating this with hand washing, the highest ICU hand washing compliance level rarely exceeds 40%. Thus, the status quo of 40% hand washing compliance equates to 1 in 20 patients acquiring a nosocomial infection.

As 60% hand washing non-compliance corresponds to a 5% increase in HAIs, 12% non-compliance correlates to an increase of 1%. Elaborating, based upon this correlation, 48% non-compliance should correlate to a 4% increase and 72% non-compliance should correlate to a rise of 6% in HAIs.

Previous data has shown that feedback and education intervention technology increase the hand washing compliance level by roughly 60%. As this compliance should be sustained, utilizing the status quo, a 40% compliance rate in the ICU should increase to 64% sustained compliance. In consideration of the above correlation, this should cause HAIs to decrease to 3% overall, corresponding to a 40% reduction. This reduction should help reduce costs in the healthcare system as well as improve quality of life, increase resource accessibility, and save lives.

Overall, the disclosed system 30 is an intervention system that aims not only to guarantee hand washing compliance, but decrease nosocomial infection rates, save lives, and save money. As healthcare costs become an increasing area of focus in the public and legislature, there is clearly no better time for such a system 30 than the present. By incrementally improving a relatively simple and intuitive system, HAIs, a preventable cost, can eventually be greatly accounted for by the disclosed system in the future.

The disclosed system 30 and method may detect, prevent and trigger the removal of environmental contamination based upon data acquired regarding healthcare personnel and hospital guest hand hygiene compliance, position and interactions within the environment of the room. The disclosed system 30 and method may monitor the interaction of healthcare personnel and guests with the patient and patient environment. The disclosed system 30 and method utilizes non-invasive sensors in order to detect deployment of sanitation equipment. The disclosed system 30 and method then couples this data with RSSI information returned from three strategically placed RFID antennas 32, 33, 34 in order to associate the act of compliance with the person 46. The disclosed system 30 and method utilizes the RSSI information returned from the three RFID antennas 32, 33, 34 in conjunction with associated time stamps in order to assess the position of the person 46 and compute and document the compliance trajectory of the person 46. The disclosed system 30 and method uses data regarding hand hygiene compliance linked with data regarding the compliance trajectory of the person 46 throughout a hospital or examination room 40 in order to identify possible contamination events. The disclosed system 30 and method is easily adaptable to different hospital room layouts and sanitation instrumentation. The disclosed system 30 and method possesses an immediate continuously variable reminder stimulus for hand hygiene compliance so as to avoid subject habituation and eventual lack of response. The disclosed system 30 and method may integrate data regarding subject hand hygiene compliance and trajectory acquired from multiple hospital rooms 40 via manipulation of all acquired data at a central database 50, in order to more accurately evaluate healthcare personnel compliance and identify potential contamination events. The disclosed system 30 and method may be implemented as a research tool in order to link lack of hand hygiene compliance with environmental contamination and transmission of nosocomial infection. The disclosed system 30 and method may be implemented as a tool to investigate and postulate means by which a patient acquired a nosocomial infection. Via the consideration of potential environmental contamination events in conjunction with subject trajectory and subsequent patient interaction, the system 30 can evaluate the source and mode of transmission of the responsible infectious pathogen. The disclosed system 30 and method may adapt to a "rounding" scenario in which multiple healthcare personnel are simultaneously present within a hospital room. The disclosed system 30 and method may not inconvenience or require modification of the present routine of healthcare personnel or hospital guests. The disclosed system 30 and method runs on sufficiently low voltage and poses minimal to no risk of interference so that it can be safely implemented in all hospital settings. The disclosed system 30 and method may provide real-time feedback to the hospital administration regarding subject hand hygiene compliance and potential contamination events. The disclosed system 30 and method may automatically alert environmental decontamination staff and/or deploy disinfection protocol. The disclosed system 30 and method may monitor and document the nurse-to-patient ratio and alert the administration when this value becomes too high, so as to minimize the risk of transmission of infectious pathogens. The disclosed system 30 and method may embody an application which manages the database server and stores all incoming data from the individual rooms. The disclosed system 30 and method may embody an application which runs on the database server and provides an interface for interacting with the data stored in the database (both in real-time and retrospectively for reviewing an incident). The disclosed system 30 and method may embody a separate application which runs on the database server and allows for administrative control over the individual rooms 40 in order to dynamically update their settings or remotely reset them.

Test Protocol and Results

Study Questions:

1. With what sensitivity and specificity can the system determine reentry?

2. With what sensitivity and specificity can the system detect an act of compliance?

3. With what sensitivity and specificity can the system detect patient contact?

4. With what sensitivity and specificity can the system detect cabinet contact?

In order to address these study questions, the following six phases of testing were performed:

Phase 1—A tagged subject walked all the way into the room and all the way back out without complying, making patient contact or making cabinet contact. System output was documented. This act was repeated for 50 successive trials.

Phase 2—A tagged subject walked to the entry of the room and lingered there for five (5) seconds, but did not enter. System output was documented. This act was repeated for 50 successive trials.

Phase 3—A tagged subject walked one foot into the room and then walked back out without complying, making patient contact or making cabinet contact. System output was documented. This act was repeated for 50 successive trials.

Phase 4—A tagged subject walked all the way into the room, complies by triggering the alcohol dispenser or soap dispenser while in the room, walks out, and complies by triggering the outside alcohol dispenser. System output was documented. This act was repeated for 50 successive trials. 25 trials involved use of the alcohol dispenser while the remaining 25 trials involved use of the soap dispenser in order to evaluate the functionality of their sensors.

Phase 5—A tagged subject walked into the room, made patient contact, and then walked out. System output was documented. This act was repeated for 100 successive trials. The subject complied for 50 trials and did not comply for 50 trials in order to assess differences in system behavior.

Phase 6—A tagged subject made cabinet contact, walked into the room and then walked out. System output was documented. This act was repeated for 100 successive trials. The subject complied for 50 trials and did not comply for 50 trials in order to assess differences in system behavior.

Test Results—the results for all six phases are provided in the following tables.

Phase I

| Trial | Entry | Exit | Compliant | Non-Compliant | No status assigned | No data | Patient Contact Recognition | Cabinet Contact Recognition |
|---|---|---|---|---|---|---|---|---|
| 1 | X | X | | | X | | | |
| 2 | X | X | | | X | | | |
| 3 | X | X | | | X | | | |
| 4 | X | X | | | X | | | |
| 5 | X | X | | | X | | X | |
| 6 | X | X | | | X | | | |
| 7 | X | X | | | X | | | |
| 8 | X | X | | | X | | | X |
| 9 | X | X | | | X | | | |
| 10 | X | X | | | X | | | |
| 11 | X | X | | | X | | | |
| 12 | X | X | | | X | | | |
| 13 | X | X | | | X | | | |
| 14 | X | X | | | X | | | |
| 15 | X | X | | | X | | | X |
| 16 | X | X | | | X | | | |
| 17 | X | X | | | X | | | |
| 18 | X | X | | | X | | | |
| 19 | X | X | | | X | | | |
| 20 | X | X | | | X | | | |
| 21 | X | X | | | X | | | |
| 22 | X | X | | | X | | | |
| 23 | X | X | | | X | | | |
| 24 | X | X | | | X | | | |
| 25 | X | X | | | X | | | |
| 26 | X | X | | | X | | | |
| 27 | X | X | | | X | | | |
| 28 | X | X | | | X | | | |
| 29 | X | X | | | X | | | |
| 30 | X | X | | | X | | | |
| 31 | X | X | | | X | | | |
| 32 | X | X | | | X | | | |
| 33 | X | X | | | X | | | |
| 34 | X | X | | | X | | | |
| 35 | X | X | | | X | | | |
| 36 | X | X | | | X | | | |
| 37 | X | X | | | X | | | |
| 38 | X | X | | | X | | | |
| 39 | X | X | | | X | | | |
| 40 | X | X | | | X | | | |
| 41 | X | X | | | X | | | |
| 42 | X | X | | | X | | | |
| 43 | X | X | | | X | | | |
| 44 | X | X | | | X | | | |
| 45 | X | X | | | X | | | |
| 46 | X | X | | | X | | | |
| 47 | X | X | | | X | | | |
| 48 | X | X | | | X | | | |
| 49 | X | X | | | X | | | |
| 50 | X | X | | | X | | | |

Phase 2

| Trial | Compliant | Non-Compliant | Linger + Departure | Linger + Entry | No data |
|---|---|---|---|---|---|
| 1 | | | X | | |
| 2 | | | X | | |
| 3 | | | X | | |
| 4 | | | X | | |
| 5 | | | X | | |
| 6 | | | X | | |
| 7 | | | X | | |
| 8 | | | | | X |
| 9 | | | X | | |
| 10 | | | X | | |
| 11 | | | X | | |
| 12 | | | X | | |
| 13 | | | | | X |
| 14 | | | | | X |
| 15 | | | | | X |
| 16 | | | X | | |
| 17 | | | | | X |
| 18 | | | X | | |
| 19 | | | X | | |
| 20 | | X | | X | |
| 21 | | | X | | |
| 22 | | | X | | |
| 23 | | | | | X |
| 24 | | | X | | |
| 25 | | | X | | |
| 26 | | | X | | |
| 27 | | | X | | |
| 28 | | | X | | |
| 29 | | | X | | |
| 30 | | | X | | |
| 31 | | | X | | |
| 32 | | | X | | |
| 33 | | | X | | |
| 34 | | | | | X |
| 35 | | | X | | |
| 36 | | | X | | |
| 37 | | | X | | |
| 38 | | | X | | |
| 39 | | | X | | |
| 40 | | | X | | |
| 41 | | | X | | |
| 42 | | | X | | |
| 43 | | | X | | |
| 44 | | | X | | |
| 45 | | | X | | |
| 46 | | | X | | |

-continued

Phase 2

| Trial | Compliant | Non-Compliant | Linger + Departure | Linger + Entry | No data |
|---|---|---|---|---|---|
| 47 | | | X | | |
| 48 | | | X | | |
| 49 | | | X | | |
| 50 | | | X | | |

Phase 3

| Trial | Entry | Exit | Compliant | Non-Compliant | No status assigned | No data | Patient Contact Recognition | Cabinet Contact Recognition |
|---|---|---|---|---|---|---|---|---|
| 1 | X | X | X | | | | | |
| 2 | X | X | X | | | | | |
| 3 | X | X | X | | | | | |
| 4 | X | X | X | | | | | |
| 5 | X | X | X | | | | | |
| 6 | X | X | X | | | | | |
| 7 | X | X | X | | | | | |
| 8 | X | X | X | | | | | |
| 9 | X | X | X | | | | | |
| 10 | X | X | X | | | | | |
| 11 | X | X | X | | | | | |
| 12 | X | X | X | | | | | |
| 13 | X | X | X | | | | | |
| 14 | X | X | X | | | | | |
| 15 | X | X | X | | | | | |
| 16 | X | X | X | | | | | |
| 17 | X | X | X | | | | | |
| 18 | X | X | X | | | | | |
| 19 | X | X | X | | | | | |
| 20 | X | X | X | | | | | |
| 21 | X | X | X | | | | | |
| 22 | X | X | X | | | | | |
| 23 | X | X | X | | | | | |
| 24 | X | X | X | | | | | |
| 25 | X | X | X | | | | | |
| 26 | X | X | X | | | | | |
| 27 | X | X | X | | | | | |
| 28 | X | X | X | | | | | |
| 29 | X | X | X | | | | | |
| 30 | X | X | X | | | | | |
| 31 | X | X | X | | | | | |
| 32 | X | X | X | | | | | |
| 33 | X | X | X | | | | | |
| 34 | X | X | X | | | | | |
| 35 | X | X | X | | | | | |
| 36 | X | X | X | | | | | |
| 37 | X | X | X | | | | | |
| 38 | X | X | X | | | | | |
| 39 | X | X | X | | | | | |
| 40 | X | X | X | | | | | |
| 41 | X | X | X | | | | | |
| 42 | X | X | X | | | | | |
| 43 | X | X | X | | | | | |
| 44 | X | X | X | | | | | |
| 45 | X | X | X | | | | | |
| 46 | X | X | X | | | | | |
| 47 | X | X | X | | | | | |
| 48 | X | X | X | | | | | |
| 49 | X | X | X | | | | | |
| 50 | X | X | X | | | | | |

Phase 4

| Trial | Entry | Alcohol Use #1 | Soap Use #1 | Compliant | Non-Compliant | No status assigned | Exit | Alcohol Use #2 |
|---|---|---|---|---|---|---|---|---|
| 1 | X | X | | X | | | X | X |
| 2 | X | X | | X | | | X | X |
| 3 | X | X | | X | | | X | X |
| 4 | X | X | | X | | | X | X |
| 5 | X | X | | X | | | X | X |
| 6 | X | X | | X | | | X | X |
| 7 | X | X | | X | | | X | X |
| 8 | X | | X | X | | | X | X |
| 9 | X | | X | X | | | X | X |
| 10 | X | | | X | | | X | X |
| 11 | | | X | X | | | X | X |
| 12 | X | | | X | | | X | X |
| 13 | X | | X | X | | | X | X |
| 14 | X | | X | X | | | X | X |
| 15 | X | X | | X | | | X | X |
| 16 | X | X | | X | | | X | X |
| 17 | X | X | | X | | | X | X |
| 18 | X | X | | X | | | X | X |
| 19 | X | X | | X | | | X | X |
| 20 | X | X | | X | | | X | X |
| 21 | X | X | | X | | | X | X |
| 22 | X | X | | X | | | X | X |
| 23 | X | | X | X | | | X | X |
| 24 | X | | X | X | | | X | X |
| 25 | X | | X | X | | | X | X |
| 26 | X | | X | X | | | X | X |
| 27 | X | X | | X | | | X | X |
| 28 | X | X | | X | | | X | X |
| 29 | X | X | | X | | | X | X |
| 30 | X | X | | X | | | X | X |
| 31 | X | X | | X | | | X | X |
| 32 | X | X | | X | | | X | X |
| 33 | X | X | | X | | | X | X |
| 34 | X | X | | X | | | X | X |
| 35 | X | X | | X | | | X | X |
| 36 | X | X | | X | | | X | X |
| 37 | X | X | | X | | | X | X |
| 38 | X | X | | X | | | X | X |
| 39 | X | X | | X | | | X | X |
| 40 | X | X | | X | | | X | X |
| 41 | X | X | | X | | | X | X |
| 42 | | X | | X | | | X | X |
| 43 | X | X | | X | | | X | X |
| 44 | X | X | | X | | | X | X |
| 45 | X | X | | X | | | X | X |
| 46 | X | X | | X | | | X | X |
| 47 | X | X | | X | | | X | X |
| 48 | X | X | | X | | | X | X |
| 49 | X | X | | X | | | X | X |
| 50 | X | X | | X | | | X | X |

Phase 5

| Trial | Compliant | Non-Compliant | Patient Contact Recognition |
|---|---|---|---|
| (Part 1) | | | |
| 1 | X | | X |
| 2 | X | | X |
| 3 | X | | X |
| 4 | X | | X |
| 5 | X | | X |
| 6 | X | | X |
| 7 | X | | X |
| 8 | X | | X |
| 9 | X | | X |
| 10 | X | | X |
| 11 | X | | X |

Phase 5

| Trial | Compliant | Non-Compliant | Patient Contact Recognition |
|---|---|---|---|
| 12 | X |   | X |
| 13 | X |   |   |
| 14 | X |   | X |
| 15 | X |   |   |
| 16 | X |   | X |
| 17 | X |   | X |
| 18 | X |   | X |
| 19 | X |   | X |
| 20 | X |   | X |
| 21 | X |   | X |
| 22 | X |   |   |
| 23 | X |   | X |
| 24 | X |   | X |
| 25 | X |   | X |
| 26 |   | X | X |
| 27 |   | X | X |
| 28 |   | X | X |
| 29 |   | X | X |
| 30 |   | X | X |
| 31 |   | X | X |
| 32 |   | X | X |
| 33 |   | X | X |
| 34 |   | X | X |
| 35 |   | X | X |
| 36 |   | X | X |
| 37 |   | X |   |
| 38 |   | X | X |
| 39 |   | X | X |
| 40 |   | X | X |
| 41 |   | X | X |
| 42 |   | X | X |
| 43 |   | X | X |
| 44 |   | X | X |
| 45 |   | X |   |
| 46 |   | X | X |
| 47 |   | X | X |
| 48 |   | X | X |
| 49 |   | X | X |
| 50 |   | X | X |

(Part 2)

| Trial | Compliant | Non-Compliant | Patient Contact Recognition |
|---|---|---|---|
| 1 | X |   | X |
| 2 | X |   | X |
| 3 | X |   | X |
| 4 | X |   | X |
| 5 | X |   | X |
| 6 | X |   | X |
| 7 | X |   | X |
| 8 | X |   | X |
| 9 | X |   | X |
| 10 | X |   | X |
| 11 | X |   | X |
| 12 | X |   | X |
| 13 | X |   | X |
| 14 | X |   | X |
| 15 | X |   | X |
| 16 | X |   | X |
| 17 | X |   |   |
| 18 | X |   | X |
| 19 | X |   | X |
| 20 | X |   | X |
| 21 | X |   | X |
| 22 | X |   | X |
| 23 | X |   | X |
| 24 | X |   | X |
| 25 | X |   | X |
| 26 |   | X | X |
| 27 |   | X | X |
| 28 |   | X | X |
| 29 |   | X | X |
| 30 |   | X | X |
| 31 |   | X | X |
| 32 |   | X | X |
| 33 |   | X | X |
| 34 |   | X | X |
| 35 |   | X | X |
| 36 |   | X | X |
| 37 |   | X | X |
| 38 |   | X | X |
| 39 |   | X | X |
| 40 |   | X | X |
| 41 |   | X | X |
| 42 |   | X | X |
| 43 |   | X | X |
| 44 |   | X | X |
| 45 |   | X | X |
| 46 |   | X | X |
| 47 |   | X | X |
| 48 |   | X | X |
| 49 |   | X | X |
| 50 |   | X | X |

Phase 6

| Trial | Compliant | Non-Compliant | Cabinet Contact |
|---|---|---|---|
| (Part 1) |   |   |   |
| 1 | X |   | X |
| 2 | X |   | X |
| 3 | X |   | X |
| 4 | X |   | X |
| 5 | X |   | X |
| 6 | X |   | X |
| 7 | X |   | X |
| 8 | X |   | X |
| 9 | X |   | X |
| 10 | X |   | X |
| 11 | X |   | X |
| 12 | X |   | X |
| 13 | X |   | X |
| 14 | X |   | X |
| 15 | X |   | X |
| 16 | X |   | X |
| 17 | X |   | X |
| 18 | X |   |   |
| 19 | X |   | X |
| 20 | X |   | X |
| 21 | X |   | X |
| 22 | X |   | X |
| 23 | X |   | X |
| 24 | X |   | X |
| 25 | X |   | X |
| 26 |   | X | X |
| 27 |   | X | X |
| 28 |   | X | X |
| 29 |   | X | X |
| 30 |   | X | X |
| 31 |   | X | X |
| 32 |   | X | X |
| 33 |   | X | X |
| 34 |   | X | X |
| 35 |   | X | X |
| 36 |   | X | X |
| 37 |   | X | X |
| 38 |   | X | X |
| 39 |   | X | X |
| 40 |   | X |   |
| 41 |   | X | X |
| 42 |   | X | X |
| 43 |   | X |   |
| 44 |   | X | X |

-continued

Phase 6

| Trial | Compliant | Non-Compliant | Cabinet Contact |
|---|---|---|---|
| 45 |  | X | X |
| 46 |  | X | X |
| 47 |  | X | X |
| 48 |  | X | X |
| 49 |  | X | X |
| 50 |  | X | X |

(Part 2)

| Trial | Compliant | Non-Compliant | Cabinet Contact |
|---|---|---|---|
| 1 | X |  | X |
| 2 | X |  | X |
| 3 | X |  | X |
| 4 | X |  | X |
| 5 | X |  | X |
| 6 | X |  | X |
| 7 | X |  | X |
| 8 | X |  | X |
| 9 | X |  | X |
| 10 | X |  | X |
| 11 | X |  | X |
| 12 | X |  | X |
| 13 | X |  | X |
| 14 | X |  | X |
| 15 | X |  | X |
| 16 | X |  | X |
| 17 | X |  | X |
| 18 | X |  |  |
| 19 | X |  | X |
| 20 | X |  | X |
| 21 | X |  | X |
| 22 | X |  | X |
| 23 | X |  | X |
| 24 | X |  | X |
| 25 | X |  | X |
| 26 |  | X | X |
| 27 |  | X | X |
| 28 |  | X | X |
| 29 |  | X | X |
| 30 |  | X | X |
| 31 |  | X | X |
| 32 |  | X | X |
| 33 |  | X | X |
| 34 |  | X | X |
| 35 |  | X | X |
| 36 |  | X | X |
| 37 |  | X | X |
| 38 |  | X | X |
| 39 |  | X | X |
| 40 |  | X |  |
| 41 |  | X | X |
| 42 |  | X | X |
| 43 |  | X |  |
| 44 |  | X | X |
| 45 |  | X | X |
| 46 |  | X | X |
| 47 |  | X | X |
| 48 |  | X | X |
| 49 |  | X | X |
| 50 |  | X | X |

Data Analysis

With regards to each of the following 2×2 tables, the columns correspond to the acts performed, while the rows detail the corresponding system output.

|  | Subject entered | Subject did not enter |
|---|---|---|
| Entry | 50 | 1 |
| No entry | 0 | 49 |

Sensitivity = 50/50 = 100%
Specificity = 49/50 = 98%

|  | Subject complied | Subject did not comply |
|---|---|---|
| Compliant | 100 | 0 |
| Non-Compliant | 0 | 100 |

Sensitivity = 100/100 = 100%
Specificity = 100/100 = 100%

|  | Patient contacted | Patient not contacted |
|---|---|---|
| Patient Contact | 94 | 1 |
| No Patient Contact | 6 | 99 |

Sensitivity = 94/100 = 94%
Specificity = 99/100 = 99%

|  | Cabinet contacted | Cabinet not contacted |
|---|---|---|
| Cabinet Contact | 96 | 2 |
| No Cabinet Contact | 4 | 98 |

Sensitivity = 96/100 = 96%
Specificity = 98/100 = 98%

The invention claimed is:

1. A system for installation into a room for occupancy by at least one patient that is receiving medical services, the room including a bed, examination table or examination chair, the room further including an entrance and at least one hand sanitization station, the system for determining whether a person, who is wearing an identification tag with radio frequency identification (RFID) data, is complying with a hand sanitization protocol before or after the person enters the room and, optionally, using this data with information regarding the person's position to identify and remedy potential contamination events, the system comprising:
a controller linked to an RFID module,
the RFID module comprising a RFID reader that is linked to a plurality of RFID antennas,
the RFID antennas for detecting the RFID from the tag as well as the position of the person in the room and transmitting to the RFID reader a received signal strength indication (RSSI) data signal including the RFID data from the tag and the position of the person in the room, the RFID reader transmitting a first signal to the controller identifying the person and the position of the person in or outside of the room,
a sensor disposed at the hand sanitization station and linked to the controller, whereby if the person engages the station, the sensor transmits a second signal to the controller,
wherein if the controller does not receive the second signal within a predetermined time period after receiving the first signal, the controller generating a reminder signal indicating that the protocol has not been complied with.

2. The system of claim 1 wherein the controller records receiving the first signal and, if generated, the reminder signal as a non-compliant event.

3. The system of claim 2 wherein the controller utilizes the noncompliant event in conjunction with information regarding subsequent interaction between the person and the patient or between the person and the room in order to identify a potential contamination event.

4. The system of claim 1 wherein, in the event the reminder signal is generated, the controller alerts administration regarding potential contamination or otherwise actives a decontamination protocol.

5. The system of claim 1 wherein in the case of the patient being infected with a nosocomial pathogen, the controller uses the RFID and RSSI data in conjunction with data regarding other hospital personnel or guest interactions with the patient and the room in order to postulate how the patient became infected with the nosocomial pathogen.

6. The system of claim 1 wherein the system is adaptable to multiple pre-existing room layouts.

7. The system of claim 1 wherein the controller records receiving the first signal and receiving the second signal as a compliant event.

8. The system of claim 1 wherein the plurality of RFID antennas includes three RFID antennas, one of which is disposed near the at least one hand sanitization station and another of which is disposed near the bed, examination table or examination chair and another of which is disposed near the entrance of the room.

9. The system of claim 1 wherein the reminder signal is selected from the group consisting of:
   illuminating a light disposed on a wall, ceiling or floor of the room;
   placing a call to a mobile phone belonging to the person;
   sending a signal to a pager assigned to the person; and combinations thereof.

10. The system of claim 1 wherein the room includes a plurality of hand sanitization stations and the system further comprises a plurality of proximity sensors, each proximity sensor being linked to the controller for transmitting a second signal to the controller.

11. The system of claim 1 wherein the first signal further comprises a time stamp.

12. The system of claim 1 wherein the controller is linked to a central computer system that records compliant and non-compliant events associated with the person.

13. The system of claim 1 wherein the room is further characterized as being selected from the group consisting of a hospital room, an outpatient surgery room, a physician's examination room, a dental office, a dining establishment or other venue that enforces a hand hygiene protocol.

14. The system of claim 1 wherein the person is further characterized as being selected form the group consisting of a physician, a dentist, a nurse, a surgeon, a medical assistant, a hospital guest, a dental assistant, a dental hygienist or other type of employee.

15. A method for determining whether a person, who is wearing an identification tag with radio frequency identification (RFID) data, is complying with a hand sanitization protocol after the person enters a room,
   the room for occupancy by at least one patient that is receiving medical services, the room including a bed, examination table or examination chair, the room further including an entrance and at least one hand sanitization station,
   the method comprising:
   when the person approaches the entrance to the room, detecting the RFID data from the tag as well as the position of the person at the entrance to the room;
   transmitting a first signal identifying the person and a current position of the person to a controller, wherein the controller is linked to a module and the module comprises a RFID reader linked to a plurality of RFID antennas, and transmitting to the RFID reader a received signal strength indication (RSSI) data signal, wherein the first signal is generated from a plurality of received signal strength indicator (RSSI) signals received by the RFID reader from a plurality of RFID antennas;
   if the person visits the hand sanitization station, detecting the presence of the person at the hand sanitization station and transmitting a second signal to the controller indicating that the person has been at the hand sanitization station;
   if the person does not visit the hand sanitization station within a predetermined time period after the first signal is transmitted, generating an audio or visual reminder;
   tracking the position of the person in the room and if the person does not visit the hand sanitization station before approaching the bed, examination table or examination chair, generating a reminder signal and as an indication of a non-compliant event; and
   optionally, linking the non-compliant event to a potential contamination event.

16. The method of claim 15 wherein if the patient is infected with a nosocomial pathogen, utilizing the RFID and RSSI data in conjunction with data regarding other hospital personnel or guest interaction with the patient and the room and postulating how the patient became infected with the nosocomial pathogen.

\* \* \* \* \*